United States Patent [19]

Suami

[11] 4,281,107

[45] Jul. 28, 1981

[54] NEAMINE DERIVATIVES AND PROCESS FOR PREPARING THE SAME

[76] Inventor: Tetsuo Suami, No. 5-8, Naka-machi 3-chome, Musashino-shi, Tokyo, Japan

[21] Appl. No.: 799,017

[22] Filed: May 20, 1977

[30] Foreign Application Priority Data

May 28, 1976 [JP] Japan .................................. 51/61247

[51] Int. Cl.$^3$ ........................................... C07H 15/22
[52] U.S. Cl. ................................. 536/17 R; 424/180; 536/4; 536/18
[58] Field of Search ........................... 536/4, 17, 17 R

[56] References Cited

U.S. PATENT DOCUMENTS 3,963,695  6/1976  Cooper ................................... 536/17

OTHER PUBLICATIONS

Suami et al. "Carbohydrate Research", vol. 53, 1977 pp. 239-246.
Rodriguez et al., "Carbohydrate Research", vol. 58, 1977 pp. 379-385.

Primary Examiner—Johnnie R. Brown
Attorney, Agent, or Firm—Sughrue, Rothwell, Mion, Zinn and Macpeak

[57] ABSTRACT

5,6-Dideoxyneamine, useful as an antimicrobial agent, and a process for preparing 5,6-dideoxyneamine.

5 Claims, No Drawings

NEAMINE DERIVATIVES AND PROCESS FOR PREPARING THE SAME

BACKGROUND OF THE INVENTION

1. Field of the Invention

This invention relates to a dideoxyneamine useful as an antimicrobial agent and a process for preparing the same. More particularly, this invention relates to 5,6-dideoxyneamine represented by the formula (I):

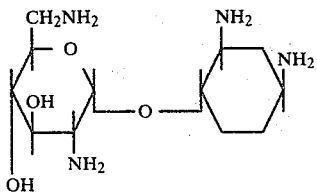

and a process for preparing 5,6-dideoxyneamine which comprises hydrogenating a compound represented by the formula (II):

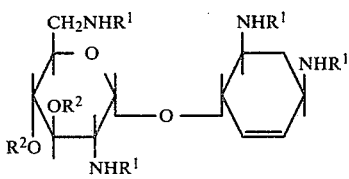

wherein $R^1$ represents a protective group for an amino group and $R^2$ represents a protective group for a hydroxyl group, and then removing the protective groups for the amino and hydroxyl groups.

2. DESCRIPTION OF THE PRIOR ART

Extensive investigations have been conducted on syntheses of antibiotics effective against antibiotic-resistant microorganisms, particularly aminocyclitol derivatives.

3',4'-Dideoxyneamine which is a 3',4'-deoxy form of neamine has hitherto been proposed, and it has been confirmed that the 3',4'-dideoxyneamine is effective against various antibiotic-resistant microorganisms as reported in *J. Antibiotics*, 24 (10), 711 (1971).

Previously, 5-deoxyneamine or 6-deoxyneamine, which is a 5- or 6-deoxy form of a deoxystreptamine moiety of neamine, was developed (as described in Japanese Patent Application No. 137,222/75 (corresponding to U.S. Patent application Ser. No. 730,396, filed Oct. 7, 1976) now U.S. Pat. No. 4,103,082) with the expectation that such a deoxy form would exhibit antimicrobial activities on antibiotic-resistant microorganisms similar to those obtained with the above described 3',4'-dideoxyneamine.

Further investigations have now been made on 5,6-dideoxyneamine and processes for preparing the same with the expectation that such a 5,6-dideoxy form would have an increased effect against antibiotic-resistant microorganisms. As a result, it has now been found that the 5,6-dideoxyneamine has unexpectedly high activity against various antibiotic-resistant microorganisms, thus accomplishing the present invention.

SUMMARY OF THE INVENTION

An object of the present invention is to provide 5,6-dideoxyneamine, having antimicrobial activities.

Another object of this invention is to provide a process for producing 5,6-dideoxyneamine.

In one embodiment of this invention, this invention provides 5,6-dideoxyneamine represented by the formula (I):

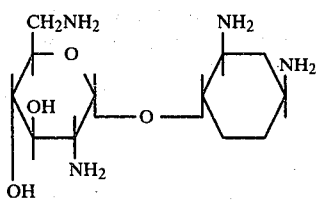

having antimicrobial activity.

In another embodiment of this invention, this invention provides a process for preparing 5,6-dideoxyneamine comprising hydrogenating a compound represented by the formula (II):

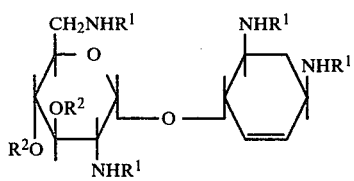

wherein $R^1$ represents a protective group for an amino group and $R^2$ represents a protective group for a hydroxyl group, and removing the protective groups for the amino group and the hydroxyl group by hydrolysis.

DETAILED DESCRIPTION OF THE INVENTION

The process for preparing 5,6-dideoxyneamine is illustrated below in the order of reaction steps.

A compound represented by the formula (II):

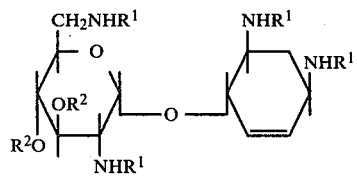

wherein $R^1$ represents a protective group for an amino group and $R^2$ represents a protective group for a hydroxyl group, is hydrogenated.

Specific examples of suitable starting compounds of the formula (II) are those having the following groups:

$R^1$: an alkoxycarbonyl group, particularly an alkoxycarbonyl group having 1 to 4 carbon atoms in the alkoxy moiety, such as a methoxycabonyl group, an ethoxycarbonyl group, a propoxycarbonyl group, an isopropoxycarbonyl group and a butoxycarbonyl group; an aryloxycarbonyl group, such as a phenoxycarbonyl group and a p-nitropenoxycarbonyl group; and an aralkoxycarbonyl group, such as a benzyloxycarbonyl group, a p-methoxybenzyloxycarbonyl group, a p-ethoxybenzyloxycarbonyl group, a p-chlorobenzyloxycarbonyl group and a p-nitrobenzyloxycarbonyl group.

$R^2$: an acyl group, such as an acetyl group, a propionyl group, and a butyryl group; an aroyl group, such as a benzoyl group, a p-chlorobenzoyl group and a p-nitrobenzoyl group; a R'—CH(OR")— group and a R'—CR"(OR''')— group wherein R', R" and R''' may be the same or different and represent a hydrocarbon chain and R' and R" may join to form a hydrocarbon ring such as a 2-tetrahydropyranyl group or a 1-methoxy-1-cyclohexyl group; an alkoxycarbonyl group, such as an ethoxycarbonyl group, t-butoxycarbonyl group and a t-amyloxycarbonyl group; and an aralkoxycarbonyl group, such as a benzyloxycarbonyl group, a p-methoxybenzyloxycarbonyl group, a p-ethoxybenzyloxycarbonyl group and a p-chlorobenzyloxycarbonyl group.

The reaction is carried out by dissolving the starting compound of the formala (II) in water, methanol, ethanol, isopropanol, acetone, dioxane, dimethylformamide, tetrahydrofuran and the like, e.g., in a concentration of about 0.5 to about 20% by weight, and bubbling hydrogen gas into the solution in the presence of a catalyst, such as Raney nickel, palladium-carbon, platinum oxide, cobalt, rhodium complexes, iron, copper and the like. The reaction is conducted at a temperature ranging from about −20° to about 130° C., preferably from room temperature (about 20°–30° C.) to about 100° C., under normal pressure or under a pressure of about 2 to about 50 kg/cm². Completion of the reaction can be monitored using thin-layer chromatography and the reaction is generally completed in about 1 to 72 hours.

The protective groups of the thus obtained dideoxy form are removed by hydrolyzing, preferably at 15° C. to 120° C., more preferably 60° C. to 100° C., the dideoxy form in a suitable solvent such as a mixture of water and a water-soluble solvent (such as methanol, ethanol, acetone, dioxane and the like) in the presence of a catalyst, such as an acid, e.g., hydrochloric acid, sufuric acid, etc., and an alkali, e.g., barium hydroxide, sodium hydroxide, potassium hydroxide, sodium alkoxides, potassium alkoxides, ammonia, hydrazine, etc., thereby obtaining 5,6-dideoxyneamine of the formala (I) above. A suitable reaction time for this step ranges from about 1 to 24 hours and completion can be monitored by thin layer chromatography.

The resulting compound can be isolated and purified by means of column chromatography using a weakly acidic ion exchange resin and the like.

The results of antimicrobial activity tests conducted on the 5,6-dideoxyneamine to demonstrate the unexpected effects obtained are shown in Table 1 below. The inhibitory activities were determined at various concentrations of the compounds using the paper disc method against the microorganisms indicated and the numerical values show the inhibition zone diameter in terms of mm.

TABLE 1

Antimicrobial Activity of 5,6-Dideoxyneamine (paper disk method; units indicate diameter (in mm) of the inhibition zone)

| Concentration (γ/ml) | Strain | | | | | | |
|---|---|---|---|---|---|---|---|
| | B. subtilis | E. coli K-12 | E. coli ML-1629 | S. aureus 6538P | S. epidermidis 12228 | Mycobac. 607 | Kleb. pneum. 7 |
| 1,000 | 33.7 | 33.0 | 10.3 | 25.6 | 27.6 | 17.3 | 22.2 |
| 500 | 31.1 | 29.0 | 0 | 22.4 | 25.2 | 11.9 | 19.4 |
| 250 | 30.1 | 25.6 | 0 | 19.6 | 22.4 | 9.4 | 16.8 |
| 125 | 26.9 | 22.0 | 0 | 15.9 | 19.8 | 0 | 13.5 |
| 62.5 | 24.4 | 19.7 | 0 | 12.0 | 17.4 | 0 | 10.0 |
| 31.2 | 22.0 | 15.6 | 0 | 0 | 14.4 | 0 | 0 |
| 15.6 | 19.7 | 13.2 | 0 | 0 | 12.7 | 0 | 0 |
| 7.8 | 17.0 | 0 | 0 | 0 | 10.9 | 0 | 0 |
| 3.9 | 14.6 | 0 | 0 | 0 | 0 | 0 | 0 |
| 1.95 | 10.2 | 0 | 0 | 0 | 0 | 0 | 0 |

TABLE 2

Antimicrobial Activity of Neamine (paper disk method; units indicate diameter (in mm) of the inhibition zone)

| Concentration (γ/ml) | Strain | | | | | | |
|---|---|---|---|---|---|---|---|
| | B. subtilis | E. coli K-12 | E. coli ML-1629 | S. aureus 6538P | S. epidermidis 12228 | Mycobac. 607 | Kleb. pneum. 7 |
| 1,000 | 33.6 | 35.0 | 0 | 25.0 | 28.0 | 20.1 | 0 |
| 500 | 30.3 | 31.0 | 0 | 21.1 | 24.6 | 13.5 | 0 |
| 250 | 29.3 | 28.8 | 0 | 18.3 | 22.0 | 0 | 0 |
| 125 | 26.3 | 24.5 | 0 | 14.6 | 19.6 | 0 | 0 |
| 62.5 | 24.1 | 21.2 | 0 | 11.2 | 16.1 | 0 | 0 |
| 31.2 | 20.8 | 18.4 | 0 | 0 | 13.6 | 0 | 0 |
| 15.6 | 18.3 | 15.3 | 0 | 0 | 11.4 | 0 | 0 |
| 7.8 | 15.2 | 11.6 | 0 | 0 | 0 | 0 | 0 |
| 3.9 | 11.1 | 0 | 0 | 0 | 0 | 0 | 0 |
| 1.95 | 0 | 0 | 0 | 0 | 0 | 0 | 0 |

As it will be seen from the results obtained above, 5,6-dideoxyneamine of this invention exhibits antimicrobial activities against Gram positive and Gram negative microorganisms superior to those of the parent neamine. Specifically, there is a tendency for the minimum inhibition concentration of 5,6-dieoxyneamine against *B.subtilis, E.Coli* ML-1629, *S.epidermidis* 12228, Mycobac. 607 and *Kleb.pneum.* 7 to be superior to those of neamine.

The compounds represented by the formula (II) which can be used in this invention are also novel compounds, and an example of the process for preparing the same is given in Reference Example 1.

Further, the 5,6-dideoxyneamine obtained in this invention can be acetylated in an organic solvent such as methanol, ethanol, pyridine, etc., with acetic anhydride to obtain the corresponding acetylated compound. An example for the acetylation is given in Reference Example 2.

The present invention will now be illustrated in greater detail by way of an Example. Unless otherwise indicated herein, all parts, percents, ratios and the like are by weight.

EXAMPLE (1) Preparation of 3',4'-Di-o-acetyl-1,3,2',6'-tetra-N-ethoxycarbonyl-5,6-dideoxyneamine 116 mg of 3',4'-di-o-acetyl-5,6-dideoxy-5-ene-1,3,2',6'-tetra-N-ethoxycarbonylneamine was reduced in 20 ml of methanol in the presence of 10 mg of platinum oxide for 15 hours using a Paar reductor (3.4 kg/cm$^2$). The catalyst was removed by filtration, and the filtrate evaporated off. The residue was dissolved in 10 ml of benzene, and hexane was added thereto to obtain 113 mg of 3',4'-di-o-acetyl-1,3,2',6'-tetra-N-ethoxycarbonyl-5,6-dideoxyneamine in a yield of 97%.

Melting Point: 61°–94° C.

$[\alpha]_D^{20}$: +78.1° (C 2.5, chloroform)

NMR Spectrum: 1.22 (t, 12H, J=7 Hz, 4COOCH$_2$C$\underline{H}_3$), 1.98 (s, 3H, OAc) and 2.01 (s, 3H, OAc).

Elemental Analysis for C$_{28}$H$_{46}$N$_4$O$_{14}$:

|  | C | H | N |
|---|---|---|---|
| Calculated (%): | 50.75 | 7.00 | 8.45 |
| Found (%): | 50.84 | 7.00 | 8.15 |

(2) Preparation of 5,6-Dideoxyneamine 302 mg of 3',4'-di-o-acetyl-1,3,2',6'-tetra-N-ethoxycarbonyl-5,6-dideoxyneamine obtained as described in (1) above was hydrolyzed in 30 ml of a methanolic solution of 3 g of barium hydroxide under reflux for 10 hours, and the product was purified using Amberlite CG-50 (NH$_4^\pm$) (trade-name produced by Rohm & Haas Co.) to obtain 74 mg (56%) of 5,6-dideoxyneamine.

Melting Point: 128°–142° C.

$[\alpha]_D^{20}$: +125°(C2.0, water)

Thin layer chromatography of the resulting product using a solvent of 28% aqueous ammonia:butanol:ethanol:water (5:8:10:7 by volume) showed a single spot (R$_f$=0.14).

REFERENCE EXAMPLE 1

(1) Preparation of 3',4'-Di-o-acetyl-1,3,2',6'-tetra-N-ethoxycarbonyl-5,6-di-mesyl-neamine 710 mg of 3',4'-di-o-acetyl-1,3,2',6'-tetra-N-ethoxycarbonyl-neamine (prepared by the method described in T. Suami, S. Nishiyama, Y. Ishikawa and S. Katsura, *Carbohydrate Research* vol. 53, page 239 (1977)) was dissolved in 4 ml of pyridine under ice-cooling, and 0.8 ml of mesyl chloride was added thereto. The reaction mixture was stirred at room temperature for 20 hours, and cool water was added to the mixture thereby precipitating crystals. The precipitated crystals were filtered and recrystallized from 2-propanol to obtain 560 mg (64%) of 3',4'-di-o-acetyl-1,3,2',6'-tetra-N-ethoxycarbonyl-5,6-di-o-mesyl-neamine.

Melting Point: 188°–189° C.

$[\alpha]_D^{21}$: +35.0° (C 0.92, chloroform).

NMR Spectrum: δ1.1–1.4 (m, 12H, 4COOCH$_2$C$\underline{H}_3$), 1.98 (s, 3H, OAc), 2.03 (s, 3H, OAc), 3.12 (s, 3H, SO$_2$CH$_3$) and 3.25 (s, 3H, SO$_2$CH$_3$).

Elemental Analysis for C$_{30}$H$_{50}$N$_4$S$_2$O$_{20}$:

|  | C | H | N | S |
|---|---|---|---|---|
| Calculated (%): | 42.34 | 5.92 | 6.58 | 7.53 |
| Found (%): | 42.36 | 5.85 | 6.21 | 7.48 |

(2) Preparation of 3',4'-Di-o-acetyl-5,6-dideoxy-5-ene-1,3,2',6'-tetra-N-ethoxycarbonyl-neamine 505 mg of the 3',4'-di-o-acetyl-1,3,2',6'-tetra-N-ethoxycarbonyl-5,6 -di-mesyl-neamine prepared as described in (1) above was stirred together with 5.0 g of sodium iodide and 2.5 g of zinc powder in 10 ml of dimethylformamide at 100° C. for 2.5 hours. The reaction mixture was diluted with 40 ml of chloroform and then filtered. The filtrate was washed successively with a saturated aqueous solution of sodium chloride, a 20% solution of thiosulfuric acid and cool water and dried over anhydrous sodium sulfate. The chloroform was evaporated off, and the residue was purified by silica gel chromatogrphay to obtain a crude product. The crude product was dissolved in 15 ml of benzene, and hexane was added thereto to obtain 169 mg of 3',4'-di-o-acetyl-5,6-dideoxy-5-ene-1,3,2',6'-tetra-N-ethoxycarbonyl-neamine as an amorphous powder in a yeild of 43%.

Melting Point: 80°–120° C.

$[\alpha]_D^{22}$: +159° (C 1.8, chloroform).

NMR Spectrum: δ1.23 (t, 12H, J=7 Hz, 4COOCH$_2$C$\underline{H}_3$), 2.00 (s, 3H, OAc), 2.02 (s, 3H, OAc), and 5.65 (s, 2H, H-5 and 6).

Elemental Analysis for C$_{28}$H$_{44}$N$_4$O$_{14}$:

|  | C | H | N |
|---|---|---|---|
| Calculated (%): | 50.90 | 6.71 | 8.48 |
| Found (%): | 51.05 | 6.74 | 8.33 |

REFERENCE EXAMPLE 2

Preparation of 1,3,2',6'-Tetra-N-acetyl-5,6-dideoxyneamine 20 mg of 5,6-dideoxyneamine prepared as described in the Example was acetylated in 1 ml of methanol with 0.05 ml of acetic anhydride at 5° C. overnight. The solution was evaporated to dryness, and the residue was washed with diethyl ether to obtain 23 mg (73%) of 1,3,2',6'-tetra-N-acetyl-5,6-dideoxyneamine.

Melting Point: higher than 280° C.

$[\alpha]_D^{20}$: +111° (C 1.0, water).

NMR Spectrum: δ1.93 (s, 3H, NAc), 1.98 (s, 3H, NAc), 2.02 (s, 3H, NAc), 2.03 (s, 3H, NAc) and 4.98 (d, 1H, J=3.5 Hz, H—1').

Elemental Analysis for C$_{20}$H$_{34}$N$_4$O$_8$ . H$_2$O:

|  | C | H | N |
|---|---|---|---|
| Calculated (%): | 50.41 | 7.62 | 11.76 |
| Found (%): | 50.34 | 7.42 | 11.44 |

While the invention has been described in detail and with reference to specific embodiments thereof, it will be apparent to one skilled in the art that various changes and modifications can be made therein without departing from the spirit and scope thereof.

What is claimed is:
1. 5,6-Dideoxyneamine.
2. A compound represented by the formula

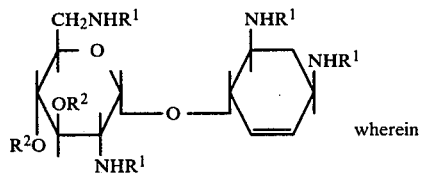

wherein

R¹ represents a member selected from the group consisting of a methoxycarbonyl group, an ethoxycarbonyl group, a propoxycarbonyl group, an isopropoxycarbonyl group, a butyoxycarbonyl group, a phenoxycarbonyl group, a p-nitrophenoxycarbonyl group, a benzyloxycarbonyl group, a p-methoxybenzyloxycarbonyl group, a p-ethoxybenzyloxycarbonyl group, a p-chlorobenzylcarbonyl group and a p-nitrobenzyloxycarbonyl group and;

R² represents a member selected from the group consisting of an acetyl group, a propionyl group, a butyryl group, a benzoyl group, a p-chlorobenzoyl group, a p-nitrobenzoyl group, a 1-methoxy-1-cyclohexyl group, a 2-tetrahydropyranyl group, an ethoxycarbonyl group, t-butoxycarbonyl group, a t-amyloxycarbonyl group, a benzyloxycarbonyl group, a p-methoxybenzyloxycarbonyl group, a p-ethoxybenzyloxycarbonyl group and a p-chlorobenzyloxycarbonyl group.

3. 5,6-Dideoxy-5-ene-neamine of the formula:

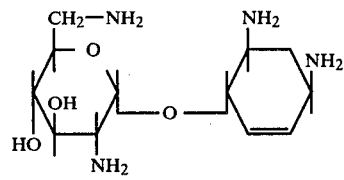

4. A process for preparing 5,6-dideoxyneamine, which comprises hydrogenating 5,6-dideoxy-5-ene-neamine whose hydroxy and amino groups are protected, and hydrolyzing the protective groups from the hydrogenated product.

5. A compound of the formula

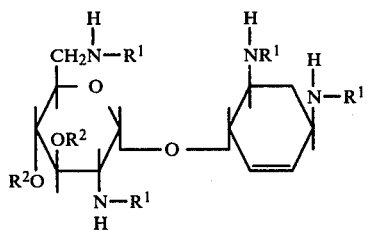

wherin R¹ is an amino protective group and R² is a hydroxyl protective group.

* * * * *